United States Patent [19]
Wong

[11] 4,357,336
[45] Nov. 2, 1982

[54] CERTAIN 2,2-DIMETHYL-3-(ETHENYL OR PROPENYL)-CYCLOPROPANE CARBOXYLIC ACID ESTERS OF THE PYRIDYL-LOWER ALKYL SERIES HAVING INSECT REPELLING PROPERTIES

[75] Inventor: Rayman Y. Wong, Richmond, Calif.

[73] Assignee: Stauffer Chemical Company, Westport, Conn.

[21] Appl. No.: 332,981

[22] Filed: Dec. 21, 1981

[51] Int. Cl.$^3$ .................... A01N 43/40; C07D 213/55
[52] U.S. Cl. .................................... 424/263; 546/342
[58] Field of Search ................. 546/341, 342; 424/263

[56] References Cited

U.S. PATENT DOCUMENTS 4,178,384 12/1979 Ensing ................................ 424/305

FOREIGN PATENT DOCUMENTS 485786 7/1980 Spain .................................. 546/341

OTHER PUBLICATIONS

Schreck et al., Chemical Abstracts, vol. 90, p. 167, No. 82, 104b (1979).

*Primary Examiner*—Alan L. Rotman
*Attorney, Agent, or Firm*—Joel G. Ackerman

[57] ABSTRACT

Compounds having the formula

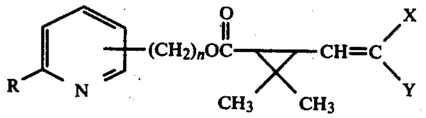

in which R is hydrogen or $C_1$–$C_4$ alkyl; X and Y are independently halogen or methyl; and n is an integer from 1 to 3, are effective insect repellents.

18 Claims, No Drawings

CERTAIN 2,2-DIMETHYL-3-(ETHENYL OR PROPENYL)-CYCLOPROPANE CARBOXYLIC ACID ESTERS OF THE PYRIDYL-LOWER ALKYL SERIES HAVING INSECT REPELLING PROPERTIES

This invention relates to novel compounds having the formula

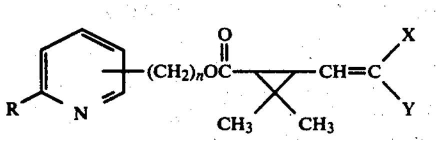

in which R is hydrogen or $C_1$–$C_4$ alkyl; X and Y are independently halogen or methyl; and n is an integer from 1 to 3. Preferably, R is hydrogen or methyl, X and Y are chlorine, bromine, fluorine, or methyl. If R is hydrogen, the side chain may be substituted on the pyridine ring at the 2-, 3-, or 4-position; if R is lower alkyl the side chain may be substituted at the 2- or 3-position.

The compounds have utility as insect repellents, particularly for repelling flying insects, especially houseflies, from lighting and/or feeding.

The compounds of this type can be prepared by reaction of an appropriate pyridyl alkanol with an appropriate acyl chloride;

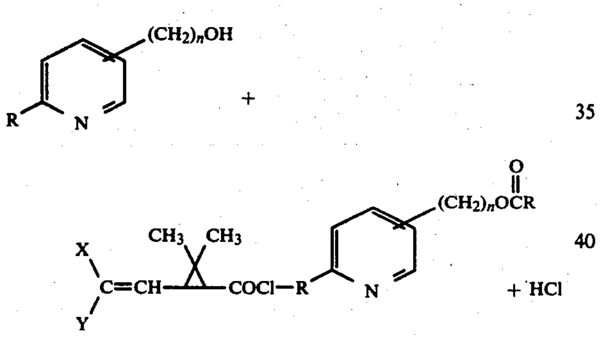

The pyridyl alkanols in which R is lower alkyl, if not commercially available, can be synthesized, for example, by the method of Umezawa et al., Japanese patent application No. 74/13180.

The reaction is generally conducted at temperatures of about 0° C. to about 25° C. in the presence of a solvent such as methylene chloride and a hydrogen chloride acceptor such as triethylamine or pyridine. The product is recovered by conventional extraction, washing, filtration, and other purification steps as may be necessary.

Preparation of such compounds is illustrated by the following example.

PRODUCTION OF 3-(3-PYRIDYL)-1-PROPYL-2,2-DIMETHYL-3-(2-METHYL-1 PROPENYL)-CYCLOPROPANE CARBOXYLATE (COMPOUND 2 HEREIN)

In a flask were mixed 5.1 grams (g.) (0.0375 mole) 3-(3-pyridyl)-1-propanol, 3.0 g. pyridine and 50 milliliters (ml.) methylene chloride and the resulting solution was cooled to 0° C. There was added 7.0 g. (0.0375 mole) 2,2-dimethyl-3-(2-methyl-1-propenyl) cyclopropane carboxylic acid chloride, at such a rate as to maintain the temperature at a maximum of about 15° C. After addition was complete, the mixture was stirred at room temperature for 3 hours.

The resulting clear yellow solution was washed with water and methylene chloride, the organic layer was separated and washed with cold 10% sodium hydroxide solution, water (to bring the pH to about 7) and saturated aqueous sodium chloride, and then dried over sodium sulfate.

The solvent was removed in vacuo from the dried solution (after filtering) to yield 8.1 g. (75.2% of theoretical yield) of a crude, clear, orange oil, which was purified by low pressure liquid chromatography, producing a liquid product having a refractive index of 1.5052. The structure of the product was confirmed by infrared (ir), nuclear magnetic (nmr) and mass spectroscopy (ms). The nmr indicated a ratio of trans to cis isomers of 73:27.

The following Table I contains a list of representative compounds of this invention.

TABLE I

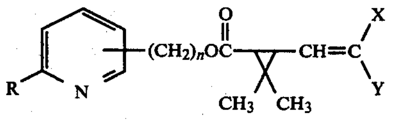

| Compound No. | Substitution On Pyridine Ring | n | R | X | Y | $n_D^{30}$ |
|---|---|---|---|---|---|---|
| 1 | 3— | 3 | H | Cl | Cl | (dark liquid) |
| 2 | 3— | 3 | H | $CH_3$ | $CH_3$ | 1.5052 |
| 3 | 3— | 1 | H | $CH_3$ | $CH_3$ | 1.5112 |
| 4 | 2— | 2 | H | $CH_3$ | $CH_3$ | 1.5071 |
| 5 | 4— | 3 | H | $CH_3$ | $CH_3$ | 1.5072 |
| 6 | 2— | 3 | H | $CH_3$ | $CH_3$ | 1.5061 |
| 7 | 2— | 3 | $CH_3$ | $CH_3$ | $CH_3$ | 1.5032 |

The structures of the compounds in the foregoing Table I were confirmed by ir, nmr, and/or ms. Because of the cyclopropane ring the compounds may exist as either the cis- or trans-isomeric form, or as racemic mixtures thereof.

INSECT REPELLENT TESTS

The compounds described in the above Table I were tested for insect repellency by the following procedures:

MOSQUITOS

A paper cup filled with pupae of the mosquito *Culex pipiens quinquefasciatus* (Say) was placed in a screened cage and the pupae allowed to emerge into adults. Sugar cubes were then saturated with 1.0 milliliter (ml.) of an acetone solution containing 0.1 wt. % of the test compound, and, for a control, with the same amount of acetone alone. After the cubes dried they were put into the screened cage. Repellency was determined by the number of mosquito adults lighting and feeding on the sugar cubes, with observations being made daily for 5 days after treatment. The number of days of complete repellency of mosquitoes from the sugar cubes was recorded.

Comparative tests were similarly conducted using the compound N,N-diethyl-m-toluamide, commercially manufactured and employed as an insect repellent, generally known by the generic name "deet." The results of the tests of deet and the compounds of Table I are shown in the following Table II. The numbers in each column represent the number of days of complete repellency observed using the specified concentration.

TABLE II

| Compound | Days Repelled, 0.1 wt. % |
|---|---|
| 1 | 3-4 |
| 2 | 3 |
| deet | 1 |
| control | 0 |

HOUSEFLIES

The insect utilized for this test was the housefly, *Musca domestica* (L.). One hundred houseflies of mixed sexes were placed in test cages. In each cage was placed a sugar cube saturated with 1.0 ml of acetone containing 1 wt. % of the test compound. The cube was dried and weighed before being placed in the cage. Each cage also contained a water-saturated cotton plug, to provide moisture. The test cages were placed on a turntable and rotated at 1.5 revolutions per minute to keep the flies randomly distributed inside the cage. After 48 hours the flies in each cage were anesthetized with carbon dioxide. The sugar cubes were removed and reweighed and the percentage weight loss (due to consumption by the flies) recorded. A repellency ratio, calculated as the percent weight loss of the treated sugar cube divided by the percent weight loss of a control sugar cube treated with acetone only was calculated. The lower the repellency ratio, the greater the repellency of the test compound. The repellency ratios of the test compounds are shown in the following Table III. Values given for the repellency ratio represent an average of from one to two replications per compound.

TABLE III

| Compound | Repellency Ratios; Concentration, 1 wt. % |
|---|---|
| 1 | 0.16 |
| 2 | 0.07 |
| 3 | 0.17 |
| 4 | 0.28 |
| 5 | 0.06 |
| 6 | 0.32 |
| 7 | 0.30 |
| deet | 0.29 |

Thus, at a concentration of 1% by weight, the test compounds repelled insects to the extent that the weight loss of sugar cubes treated with those compounds was less than 35% of that of the control (untreated) cubes.

Compound 2 also showed good repellent activity in a similarly conducted test, against the black blowfly (*Phormia irritans*).

STABLE FLY; YELLOW FEVER MOSQUITO

Insects utilized for these tests were the stable fly, *Stomoxys calcitrans* and yellow fever mosquito, *Aedes aegypti.*

Pupae of these insects were placed in separate standard fly cages and allowed to emerge into adults. The mosquitoes were supplied with a sugar-water solution; the stable flies with water, sugar cubes, and casein. Tests on mosquitoes were performed at least 3 days after the adults emerged; those on stable flies, one day after emergence because of the short life span (4–5 days) of these flies without a blood meal.

Test compounds were weighed and dissolved in acetone. One milliliter (ml) of the test solution was pipetted onto a 9×9 cm. swatch of cotton stocking. The swatches were then allowed to dry for 1 hour.

A square opening 6×6 cm. was made in an upper corner of one side of each fly cage. A large, hard cardboard disk was placed over the opening so that it could be rotated to either cover or expose the opening as desired. One-half of the disc was left intact. In the remaining half, several 6×6 cm. square openings were cut. When the intact half of this disc was located over the opening in the fly cage, this opening was effectively sealed.

Swatches of treated stocking were placed over the square holes in the disc and held in place by metal frames attached to magnetic tape.

To initiate the test, the disc was rotated so that a treated swatch became located over the opening in the cage. The palm of the tester's hand was placed over a cardboard ring, 8 cm. in diameter and 1 cm. thick. The ring acted as a spacer and protected the hand from bites which could otherwise be inflicted by the insects. A breath of air was exhaled through tubing into the opening, so that insects could be attracted to the swatch by the warm, moist air and the tester's hand. The number of insects landing on the swatch was observed, and the number probing, recorded during a 1-minute exposure. Repellency was considered to occur when 5 or fewer insects probed the swatch during the exposure.

The compounds were tested at application rates ranging from 0.1 mg/cm$^2$ of swatch downwards. The results of these tests on stable flies (SF) and yellow fever mosquitoes (YFM) are contained in Table IV.

TABLE IV

| Compound | Repellent Concentration, mg/cm$^2$ SF | YFM |
|---|---|---|
| 1 | >.10 | >.10 |
| 2 | >.10 | >.10 |
| 3 | >.10 | >.10 |
| 4 | >.10 | >.10 |
| 5 | >.10 | >.10 |
| 6 | >.10 | >.10 |
| 7 | >.10 | >.10 |

The novel compounds of this invention may be used as insect repellents in either diluted or undiluted form. When used in a diluted form, the compounds may be embodied in compositions containing relatively high or relatively low concentrations of the active compound. For example, the active compound can be incorporated into relatively high concentration compositions such as wet sprays or solutions in alcohol or other suitable solvents. Such compositions may contain, in addition to the active compound, adjuvants such as emulsifying agents, surface active agents, anti-oxidants and propellants which may be found normally in insect repellent preparations. The active compounds of this invention may be employed as the sole active component of such compositions or may be used in admixture with other compounds having a similar or different utility. For example, the compounds may be incorporated into creams, lotions, powders, suntan oil, insecticides and other preparations which may contain pesiticidal or other useful substances, as well as into compositions of various types used for treating fabrics or articles of clothing to render them insect repellent. In general, compositions for repellent use may contain from 0.5 to up to 80 weight %, preferably from 2 to about 40 weight %, of the novel active compounds. High concentration formulations, containing up to 95% of the compounds, could also be utilized for low-volume spraying from the air.

Examples of typical formulations employing compounds of this invention are for instance,

EXAMPLE 1: EMULSIFIABLE CONCENTRATE

| Component | Weight % |
|---|---|
| Compound 1 | 53.6 |
| Aromatic Hydrocarbon Solvent | 36.4 |
| Emulsifier | 10.0 |
| Total | 100.0 |

EXAMPLE 2: LOTION

| Component | Weight % |
|---|---|
| Compound 3 | 10.7 |
| Lanolin | 4.8 |
| Mineral oil | 8.0 |
| Trihydroxyethylamine stearate | 1.8 |
| Glycosterin | 0.8 |
| Glycerine | 4.6 |
| Sodium benzoate | 1.0 |
| Water | 68.3 |
| Total | 100.0 |

EXAMPLE 3: ALCOHOL SOLUTION

| Component | Weight % |
|---|---|
| Compound 4 | 53.6 |
| Isopropanol | 46.4 |
| Total | 100.0 |

EXAMPLE 4: ALCOHOL SOLUTION

| Component | Weight % |
|---|---|
| Compound 5 | 80.0 |
| Ethanol | 20.0 |
| Total | 100.0 |

EXAMPLE 5: WETTABLE POWDER

| Component | Weight % |
|---|---|
| Compound 7 | 26.9 |
| Hydrated calcium silicate | 62.1 |
| Sodium lignosulfonate | 5.0 |
| Orzan A (mixture of ammonium lignosulfonate and wood sugars) | 5.0 |
| Wetting agent | 1.0 |
| Total | 100.0 |

What is claimed is:

1. A compound having the formula

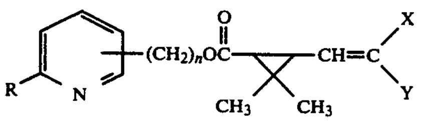

in which R is hydrogen or $C_1$–$C_4$ alkyl; X and Y are independently halogen or methyl; and n is an integer from 1 to 3.

2. A compound according to claim 1 in which n is 3.

3. A compound according to claim 1 in which R is hydrogen.

4. A compound according to claim 3 in which X and Y are both chlorine, n is 3 and the side chain is substituted on the pyridine ring at the 3-position.

5. A compound according to claim 3 in which X and Y are both methyl.

6. A compound according to claim 5 in which n is 3 and the side chain is substituted on the pyridine ring at the 3-position.

7. A compound according to claim 5 in which n is 1 and the side chain is substituted on the pyridine ring at the 3-position.

8. A compound according to claim 5 in which n is 2 and the side chain is substituted on the pyridine ring at the 2-position.

9. A compound according to claim 5 in which n is 3 and the side chain is substituted on the pyridine ring at the 4-position.

10. A compound according to claim 5 in which n is 3 and the side chain is substituted on the pyridine ring at the 2-position.

11. A compound according to claim 1 in which R, X and Y are each methyl, n is 3 and the side chain is substituted on the pyridine ring at the 2-position.

12. A method of repelling insects from a locus to be protected therefrom, comprising applying to said locus an effective insect repelling amount of a compound having the formula

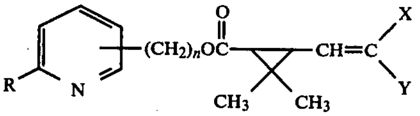

in which R is hydrogen or $C_1$–$C_4$ alkyl; X and Y are independently halogen or methyl; and n is an integer from 1 to 3.

13. A method according to claim 12 in which the compound is applied to an amount effective to repel houseflies.

14. A method according to claim 12 in which n is 3.

15. A method according to claim 12 in which R is hydrogen.

16. A method according to claim 12 in which X and Y are both chlorine.

17. A method according to claim 12 in which X and Y are both methyl.

18. An insect repellent composition comprising (a) an effective amount of a compound having the formula

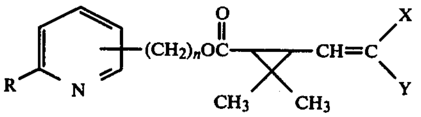

in which R is hydrogen or $C_1$–$C_4$ alkyl; X and Y are independently halogen or methyl; and n is an integer from 1 to 3, effective to repel insects, and;

(b) an inert diluent or carrier.

* * * * *